United States Patent [19]
Day et al.

[11] Patent Number: 5,269,034
[45] Date of Patent: Dec. 14, 1993

[54] SURGICAL HEAD CLAMP

[75] Inventors: James L. Day; Charles Dinkler, both of Cincinnati, Ohio

[73] Assignee: Ohio Medical Instrument Company, Inc.

[21] Appl. No.: 995,068

[22] Filed: Dec. 22, 1992

[51] Int. Cl.⁵ .............................................. A61G 7/06
[52] U.S. Cl. .......................................... 5/637; 5/622; 5/640; 5/643; 403/59; 403/83
[58] Field of Search ................. 5/622, 637, 640, 643; 602/18; 606/54; 403/59, 83, 86

[56] References Cited

U.S. PATENT DOCUMENTS

| | | | |
|---|---|---|---|
| 3,099,441 | 7/1963 | Rils | 5/637 |
| 3,835,861 | 9/1974 | Kees, Jr. et al. | |
| 4,169,478 | 10/1979 | Hickman | |
| 4,256,112 | 3/1981 | Kopf et al. | 5/637 X |
| 5,108,213 | 4/1992 | Shields | 403/59 X |

Primary Examiner—Michael F. Trettel
Attorney, Agent, or Firm—Richard H. Evans; C. Richard Eby

[57] ABSTRACT

A surgical head clamp having a C-shaped frame with a fixed head engaging pin on one side and a pair of head engaging pins on the opposite side. The opposite side of the clamp also has a rotation mechanism for adjusting the angular position of the pair of head engaging pins and a translation mechanism for linearly moving the pair of head engaging pins with respect to the fixed head engaging pin.

13 Claims, 3 Drawing Sheets

SURGICAL HEAD CLAMP

BACKGROUND OF THE INVENTION

1. Field of the Invention

This invention relates to a surgical head clamp, and more particularly, to a surgical head clamp wherein the means for axially adjusting, rotating and locking the head engaging pins are all on the same side of the clamp.

2. The Problem in the Art

Hickmann U.S. Pat. No. 4,169,478, issued Oct. 2, 1979, shows a surgical head clamp having a C-shaped frame. A first head engaging pin is mounted in a pin holder threaded into one side of the frame. Two other head engaging pins are mounted on the ends of a rotatable bracket, or clevis, on the opposite side of the frame. An adjustment knob is connected to the rear (outer end) of the pin holder. Turning the knob translates the first pin axially, thereby adjusting the distance between the first and the other opposed pins to facilitate clamping a patient's head at the three points defined by the pin points. The clevis holding the second and third pins is selectively rotatable about an axis of rotation which is coaxial with the longitudinal axis of the first pin. Selective rotation of the clevis about this axis permits the surgeon to adjust the angular relationship between the frame and the patient's head. The clevis also rotates about a transverse axis, so that the pins on the clevis can accommodate varying geometries of the head.

The Hickmann design has been found to present certain limitations in use: First, the bulkiness of the end of the clamp having the single pin and adjusting screw may hamper the surgeon's preferred hand positions or may tend to limit his access to a head location adjacent the knob.

Second, adjusting the position of the single pin to secure the patient's head in the clamp, should, ideally, result in equal clamping forces being applied by all pins. However, a skull is not a rigid body and will experience different deformations; and there will be variations from patient to patient depending on the location of the applied forces. Therefore, as the single pin is tightened and it applies a force against the patient's head, the distribution of the reactive forces by the opposite two pins is somewhat unpredictable and may be unequal; and therefore, one of opposing two pins may seat with substantially less force than the other one.

SUMMARY OF THE INVENTION

To overcome the disadvantages of the surgical head clamp of the type referred to above, a primary object of the present invention is to provide a surgical head clamp wherein all the adjusting means for the head engaging pins are located on the same side of the clamp.

According to the principles of the present invention, a surgical head clamp has a frame with a first head engaging pin mounted on a first side (leg) of the frame. Unlike prior clamps, however, no mechanism for adjusting the position of that pin is provided. Second and third head engaging pins are rotatably supported on a clevis on the opposite or second side of the frame with a rotational positioning mechanism for adjusting the angular position of the second and third head engaging pins with respect to the frame. With the present invention, a mechanism for axially translating the second and third head engaging pins is also located on the second side of the frame.

Providing all head engaging pin position adjustments on the same, single side of the clamp has an advantage of permitting the other side of the clamp, which holds the single pin, to be substantially smaller in size, thereby reducing the potential for interference with the surgeon's field. The present invention has a further advantage in that the forces generated in tightening the clamp on a patient's head are applied directly by the two pins mounted on the clevis. The single pin is now supplying the reactive force and therefore, there is a higher probability that the clevis mounted pins will apply substantially equal forces. Further, the clamp arms are preferably angled, which improves their rigidity; and therefore, they may have a smaller cross-sectional area than prior clamps thereby reducing their weight.

These and other objects and advantages of the present invention will become more readily apparent during the following detailed description taken in conjunction with the drawings herein.

DETAILED DESCRIPTION

Figure 1:
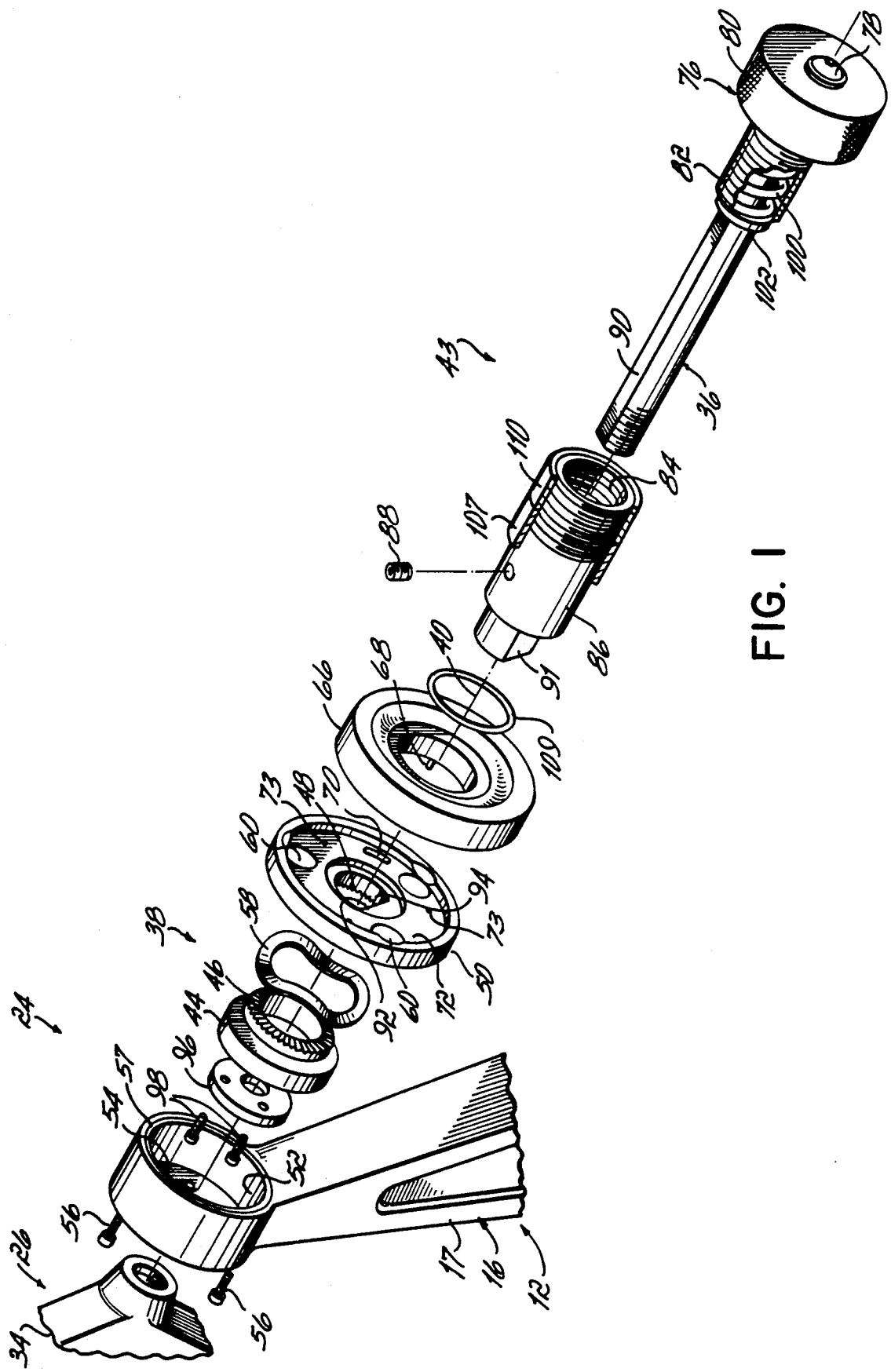
FIG. 1 is an exploded perspective view of the pin rotating, translating, and locking structure of a surgical head clamp in accordance with a preferred embodiment of the invention.
Figure 2:
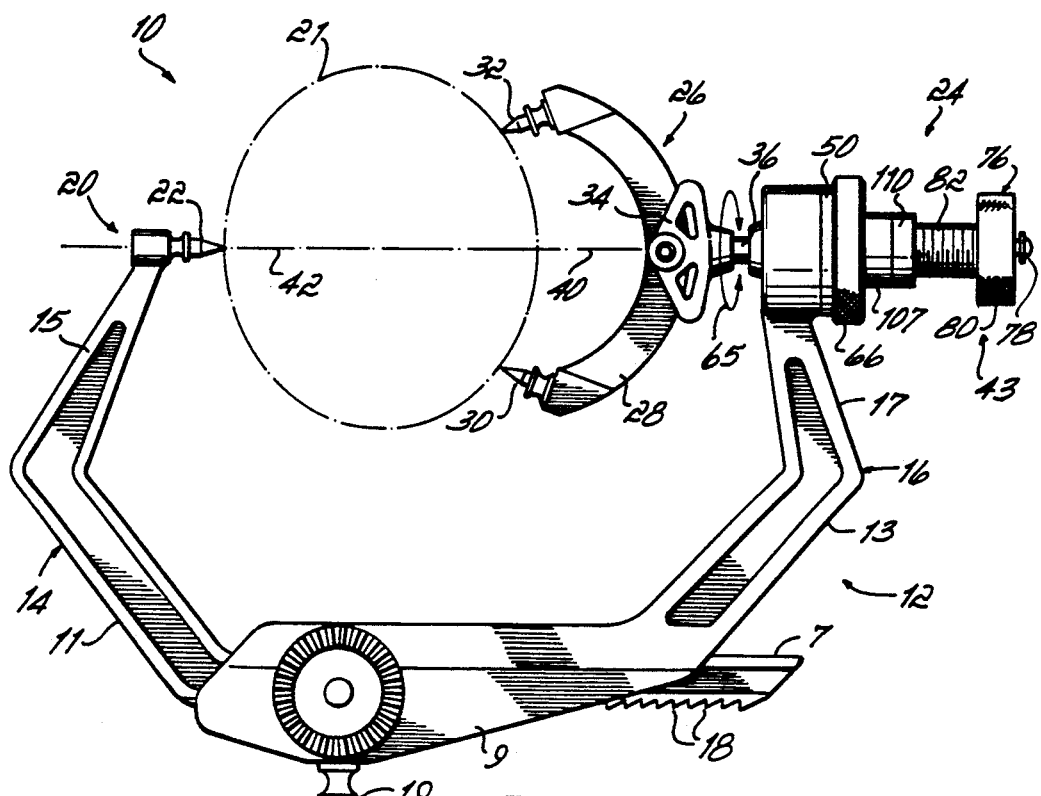
FIG. 2 is a side elevation of the surgical head clamp showing a patient's head in phantom.

The operation of the surgical head clamp of the present invention will be described with regard to FIGS. 1 through 4. The surgical head clamp 10 includes a C-shaped frame 12 comprised of frame members 14 and 16 which are movable toward and away from one another or "telescope". Frame members 14 and 16 have first arms 7 and 9, respectively, which are juxtaposed to each other in an interfitting, sliding relationship. Extending from one end of the first arm 7, frame member 14 has a lower arm 11 extending diagonally away from frame member 16 and an upper arm 15 extending angularly back toward frame member 16. Similarly, extending from first arm 9, frame member 16 has a lower arm 13 extending away from frame member 14 and an upper arm 17 extending toward frame member 14. The angled geometry of frame members 14 and 16 maintains frame rigidity and, at the same time, permits the frame members to be physically smaller than if each of the frame members were L-shaped.

One end 20 of frame member 14 preferably has only the minimum size necessary to receive and support a first head engaging pin 22. Therefore, the end 20 of the clamp 10 presents minimal potential for interference with the surgeon and the operating procedure.

The first arm 7 of frame member 14 slides within arm 9, and has rack teeth 18 which mate with a pawl 19 mounted in arm 9. The pawl 19 is spring mounted so that it is biased into contact with the rack teeth 18. The engagement of teeth 18 with pawl 19 permits frame member 14 to be slid past the pawl 19 toward frame member 16 (to the right in FIG. 2), to size or position the clamp 10 generally with respect to a patient's head 21, shown in phantom in FIG. 2. When a desired width or spacing is obtained, pawl 19 engages one of the rack teeth 18, thereby prohibiting frame member 14 from being moved away from frame member 16. Pawl 19 must be manually withdrawn against the spring force to disengage it from the rack teeth 18 in order to separate frame members 14 and 16.

An opposite end 24 of the clamp 10 has a dual pin holding means 26 which is mounted for rotation relative to frame member 16. More specifically, the pin holding means 26 includes a clevis, or bracket, 28 which receives at its ends a second head engaging pin 30 and a third head engaging pin 32. The patient's head 21 is secured in the clamp 10 by and between the first, second and third head engaging pins 22, 30 and 32, respectively, which are pressed into the head on opposite sides thereof. The clevis 28 is mounted in a clevis support 34 for rotation about an axis transverse to the plane of the clevis support. The support 34 is connected to one end of a rod, or shaft, 36.

The clamp 10 includes an angular positioning mechanism 38 for releasably locking the pin holding clevis in selected angular (rotational) positions around an axis of rotation 40 which is coaxial with a longitudinal axis 42 of pin 22. The clamp also includes a translation mechanism 43 for linearly (axially) moving the pin holding means 26 longitudinally along the axis of rotation 40.

As best shown in FIG. 1, angular positioning mechanism 38 comprises a first locking ring 44 having interlocking means preferably in the form of teeth 46 on an end face thereof, which are engagable with teeth 48 of a second locking ring 50. The end 24 of clamp frame member 16 has a bore or recess 52 which is closed at its end 54. A bushing 57 is fitted into bore 52 and is sized to receive locking rings 44 and 50. The bushing 57 maintains the locking rings 44 and 50 in coaxial alignment as locking ring 50 is translated with respect to locking ring 44. The first locking ring 44 is immovably secured in the end 54 of the clamp frame member 16, as by screws 56. A wave washer, or corrugated spring, 58 is located between the locking rings 44 and 50, and tends to bias them apart and out of interlocking engagement.

Figure 3:
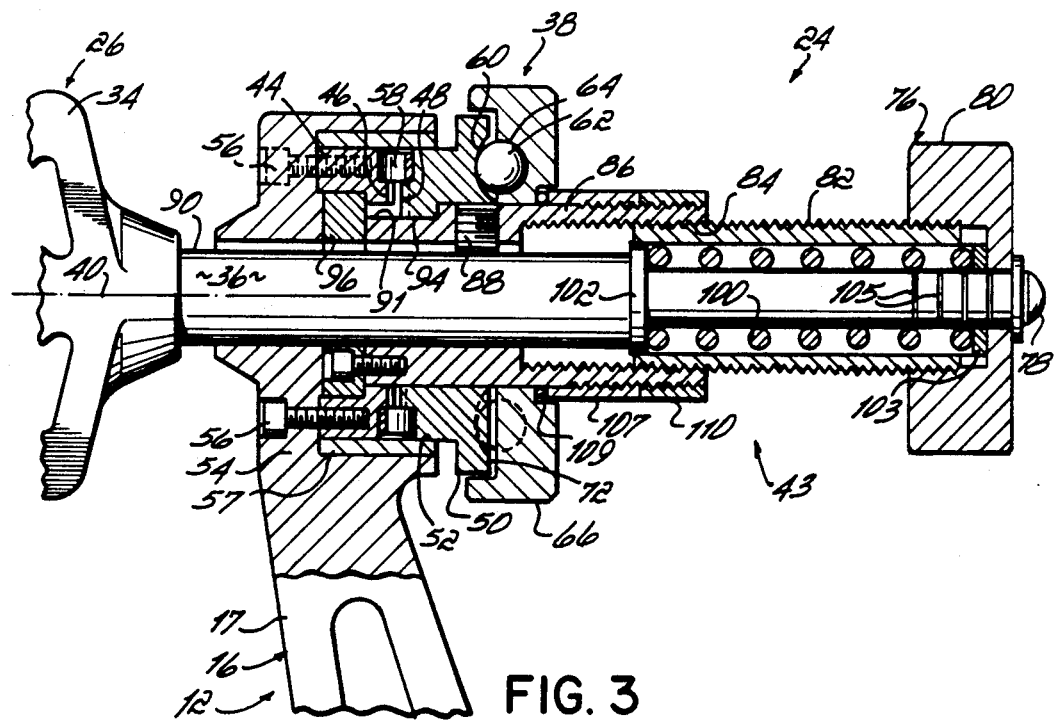
FIG. 3 is an enlarged axial cross-sectional view of the pin adjusting mechanism, illustrating the angular position locking mechanism disengaged or unlocked.

Locking ring 50 contains several detents, or recesses, 60 in its face. Balls 62, sized to be received in detents 60, are held captured in sockets 64 of operating ring 66 (FIG. 3). The sockets 64 preferably have a depth slightly greater then the radius of the balls 62 so that the balls remain in the sockets 64 as the operating ring 66 is rotated with respect to locking ring 50. Spring 58 tends to bias teeth 46 and 48 out of engagement, thereby permitting ring 66 to be rotated with respect to frame member 16.

The axial position of operating ring 66 is fixed, relative to frame end 24, but it has two operable, rotational positions relative to the second locking ring 50. In a first position as shown in FIG. 3, the operating ring 66 has an angular position relative to locking ring 50 such that the balls 62 are seated in the respective detents 60 of locking ring 50. This relieves the compression of spring 58, which pushes teeth 48 of locking ring 50 out of engagement with the teeth 46 of locking ring 44. Consequently, pin holding means 26 and shaft 36 are free to rotate about the axis of rotation 40 with respect to the frame members 14 and 16. This permits the position of the patient's head 21 to be changed, relative to clamp 10, as indicated by arrow 65 in FIG. 2.

Figure 4:
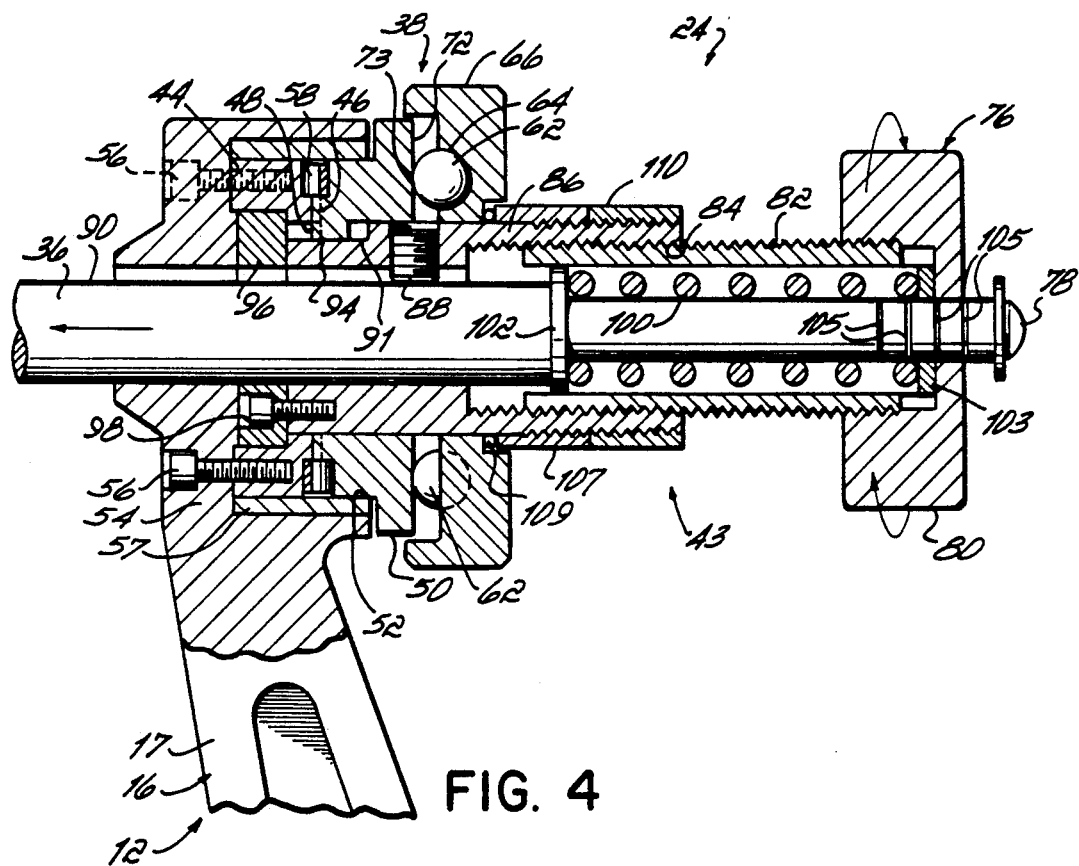
FIG. 4 is an axial cross-sectional view similar to FIG. 3 but illustrates the angular position locking mechanism in its engaged or locked position.

When the patient's head 21 has been turned to a desired angular position, the operating ring 66 is turned to a second position relative to locking ring 50. In this position, the balls 62 are twisted out of the detents 60, across the relatively "raised" flat surface 72 of locking ring 50 and into dimples 73 on the flat surface 72, as shown in FIG. 4. The surgeon feels a stop position when the balls 62 locate and seat in the dimples 73. In this position, the balls push locking ring 50 toward locking ring 44 (to the left in FIG. 4), compressing spring 58 and engaging teeth 48 of locking ring 50 with the teeth 46 of locking ring 44. Therefore, the desired angular position of the pin holding mechanism and head are locked with respect to the axis of rotation 40. The total angular movement of the operating ring 66 with respect to the locking ring 50 is mechanically limited by a pin 68 on operating ring 66 which moves in a short slot 70 on locking ring 50 (FIG. 1). An angular movement of about 30° has been found to be preferable.

Independent longitudinal (axial) motion of the pin holding mechanism 26 is generated by a translation mechanism 43 operating in conjunction with the angular positioning mechanism 38. An operating handle or knob 76 is rotatably mounted on the opposite end of the rod 36, as by a screw 78, so that knob 76 is free to rotate relative to shaft 36. The knob 76 is comprised of a knurled member 80 rigidly connected to a first threaded sleeve member 82. The sleeve member 82 is threadedly engaged into an internal bore 84 of a rotator sleeve 86. The rotator sleeve 86 is coupled to the rod 36 by a set screw 88 slidably engaging a flat surface 90 on the rod 36. The screw 88 splines or keys the sleeve 86 to shaft 36 so that rotation of the sleeve 86 transmits to the shaft 36, but shaft 36 can shift or translate axially with respect to the screw 88 and sleeve 86. In addition, a flat surface 91 at one end of the sleeve 86 cooperates with a flat surface 92 within an axial bore 94 of the second locking ring 50 (best shown in FIG. 1). A retainer plate 96 is secured to the sleeve 86, as by screws 98, so as to hold the assembly of the locking rings 44 and 50 and rotator sleeve 86 together in an operable relationship.

When the angular positioning mechanism 38 is disengaged (FIG. 3), the pin holding mechanism 26, shaft 36, second locking ring 50 and sleeve 86 can be rotated about the axis 40 as a single unit. Similarly, those elements are held in the desired angular position when the angular positioning mechanism 38 is engaged. Rotation of the knob 80 advances it and shaft 36 with respect to sleeve 86 and causes a translation along the axis of rotation 40 of the knob 76, rod 36 and pin holding means 26 toward or away from frame member 16. Therefore, the pin holding means 26 may be linearly adjusted with respect to the pin 22 independently of the operation and state of engagement of the angular position mechanism 38. The pins can be advanced angularly whether or not the locking mechanism is locked.

A helix coil spring 100 is located about the rod 36 and is supported between a flange, or shoulder, 102 on the rod 36 and a bearing washer 103 adjacent the knurled member 80. The spring 100 permits the surgeon to measure and control the forces applied by the second and third head engaging pins 30 and 32 to the patient's head 21. After the pins contact the head, continued rotation of the knob 76 will result in continued translation of the knob rod 36 and pin holding means 26 which is effective to compress the spring 100. With continued rotation of the knob 76, the spring compresses; and the shaft 36 extends beyond the knob 76, i.e., to the right, as shown in FIG. 4. Therefore, the force applied to the patient's head 21 by the head engaging pins is determined by the spring constant of the spring 100. The shaft 36 contains a scale, or markings, 105 so that the clamping force may be controlled by the surgeon. Typically, each line on the scale 105 represents about 20 pounds of force.

A locking collar, or nut, 107 is threadedly engaged on an outer surface of rotator 86. The collar 107 positions the operating ring 66 at a desired axial location along the axis 40. A bearing ring 109 is effective to reduce the rotational friction between the operating ring 66 and the first locking collar 107. Rotation of the first locking collar 107 permits the proper adjustment of engagement of the teeth 46 and 48 on locking rings 44 and 50, respectively. Once that adjustment has been made, a second locking collar, or nut, 110, also threadedly engaged on the outer surface of sleeve 86, is tightened until it is securely engaged against the first locking collar 107 thereby preventing inadvertent rotation of the first locking collar 107.

While the invention has been illustrated in some detail according to the preferred embodiments shown in the accompanying drawings and while the preferred embodiments have been described in some detail, there is no intention to thus limit the invention to such detail. On the contrary, it is intended to cover all modifications, alterations, and equivalents falling within the spirit and scope of the appended claims.

What is claimed is:

1. A surgical head clamp for supporting a patient's head comprising:
   a frame;
   a first head engaging pin secured to one side of said frame;
   pin holding means rotatably mounted to an opposite side of said frame and supporting second and third head engaging pins mounted on said pin holding means;
   means mounted on said opposite side of said frame and operably connected to said pin holding means for releasably locking said pin holding means in selected angular positions with respect to an axis of rotation of said pin holding means; and
   means mounted on said opposite side of said frame and operably connected to said pin holding means for moving said pin holding means longitudinally with respect to said axis of rotation and said first head engaging pin.

2. The surgical head clamp of claim 1 wherein said means for moving said pin holding means operates independently of said means for releasably locking said pin holding means in selected angular positions.

3. The surgical head clamp of claim 2 wherein said means for moving said pin holding means further comprises yieldable means for controlling forces applied to the patient's head by said second and third pins in response to said means for moving said pin holding means continuing to move said second and third pins after said second and third pins contact the patient's head.

4. The surgical head clamp of claim 2 wherein said means for releasably locking said pin holding means in selected angular positions further comprises
   interlockable first and second locking members; and
   means for selectively moving said first and second locking members out of interlocking engagement with one another, thereby permitting said pin holding means to be rotated, and into engagement with one another, thereby fixing the selected angular position of said pin holding means with respect to said axis of rotation.

5. The surgical head clamp of claim 4 wherein the means for moving said pin holding means further comprises
   a first member coupled to said means for releasably locking the pin holding mean; and
   a rod having one end connected to said pin holding means and translatably mounted with respect to said first member, whereby said rod and said pin holding means can translate with respect to said frame and maintain the selected angular position with respect to said axis of rotation.

6. The surgical head clamp of claim 5 wherein said first member is a sleeve rotatably coupled to said rod.

7. The surgical head clamp of claim 6 wherein said means for moving said pin holding means further comprises a knob engaged with said sleeve and rotatably connected to an opposite end of said rod whereby rotation of said knob causes said knob, said rod, said pin holding means and said second and third head engaging pins to translate with respect to said sleeve and said frame independent of and without changing a selected angular position of said pin holding means.

8. The surgical head clamp of claim 7 wherein said first locking member is connected to said frame and said second locking member is coupled to said sleeve.

9. The surgical head clamp of claim 6 wherein said rod has a first surface and said first member includes means for slidably engaging said first surface of said rod, thereby allowing said rod to translate with respect to said first member and locking said rod and said first member for rotation with respect to said axis of rotation.

10. The apparatus of claim 8 wherein said sleeve includes a second surface at one end of said sleeve cooperating with a third surface within an axial bore of said second locking member thereby causing said sleeve and said second locking member to rotate in unison about the axis of rotation.

11. The apparatus of claim 10 wherein the apparatus further comprises means in mechanical communication between said sleeve and said second locking member for adjusting the axial position along the axis of rotation of the second locking member with respect to said first locking member.

12. The apparatus of claim 11 wherein the apparatus further comprises a spring means located between said rod and said knob for applying a spring force axially with respect to said axis of rotation, whereby upon said head engaging pins contacting the patient's head, continued translation of said second and third pins to toward said first pin applies forces against the patient's head determined by a spring constant of said spring means.

13. The apparatus of claim 12 wherein said opposite end of said rod contains circumferential lines, said circumferential lines being separated by a distance correlating to forces defined by said spring constant, whereby continued translation of said second and third pins toward said first pin causes said opposite end of said rod to protrude beyond an end of said knob by a distance corresponding to the spring constant force applied by said spring means.

* * * * *